United States Patent [19]
Gallus et al.

[11] Patent Number: 6,140,382
[45] Date of Patent: *Oct. 31, 2000

[54] PROCESS FOR THE PREPARATION OF ISOCYANATES OR ISOCYANATE MIXTURES USEFUL FOR THE PREPARATION OF POLYURETHANE FOAMS

[75] Inventors: Manfred Gallus; Herbert Gebauer; Otto Immel, all of Krefeld, Germany

[73] Assignee: Bayer Aktiengesellschaft, Leverkusen, Germany

[ * ] Notice: This patent is subject to a terminal disclaimer.

[21] Appl. No.: 08/031,793

[22] Filed: Mar. 15, 1993

[30] Foreign Application Priority Data

Mar. 16, 1992 [DE] Germany .............................. 42 08 359

[51] Int. Cl.$^7$ ..................................................... C08G 18/70
[52] U.S. Cl. ........................... 521/155; 560/352; 560/353
[58] Field of Search .................................. 560/352, 353; 521/155

[56] References Cited

U.S. PATENT DOCUMENTS

| | | | |
|---|---|---|---|
| 4,465,639 | 8/1984 | Hatfield, Jr. | 260/453 PH |
| 4,774,357 | 9/1988 | Keggenhoff et al. | 560/352 |
| 4,876,380 | 10/1989 | Chen et al. | 560/352 |

FOREIGN PATENT DOCUMENTS

| | | |
|---|---|---|
| 2038126 | 9/1991 | Canada . |
| 372993 | 6/1990 | European Pat. Off. . |
| 1568623 | 4/1970 | Germany . |
| 2207671 | 7/1988 | United Kingdom . |

*Primary Examiner*—Rachel Gorr
*Attorney, Agent, or Firm*—Joseph C. Gil; Lyndanne M. Whalen

[57] ABSTRACT

Isocyanates or isocyanate mixtures which are substantially free of color-imparting components are made by treating the isocyanate with hydrogen in the presence of a catalyst at a pressure of from about 3 to about 150 bar, a temperature of from about 100 to about 180° C. for from about 15 minutes to about 4 hours. These isocyanates are particularly useful for the preparation of light-colored polyurethane rigid foams.

16 Claims, 1 Drawing Sheet

PROCESS FOR THE PREPARATION OF ISOCYANATES OR ISOCYANATE MIXTURES USEFUL FOR THE PREPARATION OF POLYURETHANE FOAMS

BACKGROUND OF THE INVENTION

The present invention relates to a process for the preparation of isocyanates or isocyanate mixtures which are substantially free of color-imparting components and their use for the preparation of light-colored polyurethane rigid foams.

The effect of color on a polyurethane rigid foam is the basis of many experiments and papers. The lightest possible yellow to white shades are desired. In addition to a better visual impression, light-colored foams indicate that the raw materials from which they were produced have a high degree of purity. Undesirable streaks are formed on the surface of rigid foams if the starting materials are dark yellow or greyish. These streaks are produced by rising during the foaming process. The precise composition of the dyes or color-imparting components in polymers which cause discoloration of polyurethane foam has not yet been proven.

As the literature shows, elimination of the color problem is an essential part of isocyanate preparation. A number of processes to improve the color of polyurethane foams are described in the prior art. The use of dried magnesium silicates to remove traces of "color-imparting impurities" in diisocyanatodiphenylmethane (MDI) at about 190° C. is disclosed in GB-A 2,207,671. In U.S. Pat. No. 4,465,639, the dark colored material produced on separation of the solvent during the preparation of diisocyanato-diphenylmethane is reduced by the addition of small amounts of water. In U.S. Pat. No. 4,876,380, an extraction process in which the polyisocyanates are separated into a purified fraction with greatly improved color and a fraction where color is not a critical requirement is disclosed. This separation is achieved by using methylene dichloride and pentane. EP 0133538 also describes the purification of polyisocyanates by extraction. EP 0446781 A1 discloses a method for improving polyurethane foam in which diaminodiphenylmethane (MDA) is subjected to a catalytic hydrogenation in the presence of a hydrogenating catalyst and a particular amount of water. All catalysts known to be useful for catalytic hydrogenation are taught to be suitable as hydrogenating catalysts in this process. By-products are produced by this hydrogenation process. These by-products remain in the MDA and lead to color-imparting impurities in the MDI under unfavorable conditions for phosgenation. In addition, it is generally known that production of intensely colored compounds in the ppm range cannot be excluded due to the phosgenation reaction itself.

SUMMARY OF THE INVENTION

It is an object of the present invention to provide a process for the preparation of isocyanates or isocyanate mixtures in which substantially no color-imparting components are present.

It is also an object of the present invention to provide a process for the production of pale-colored polyurethane foams from isocyanates which are substantially free of color-imparting components.

It is another object of the present invention to provide a process for the production of isocyanates which are substantially free of color-imparting properties and which have retained their other chemical and physical properties such as the NCO content and viscosity.

These and other objects which will be apparent to those skilled in the art are accomplished by treating the phosgenation product of one or more amines with hydrogen under a pressure of from about 3 to about 150 bar at a temperature of from about 100 to about 180° C. for from about 15 minutes to about 4 hours in the presence of a catalyst.

DETAILED DESCRIPTION OF THE INVENTION

Figure 1:
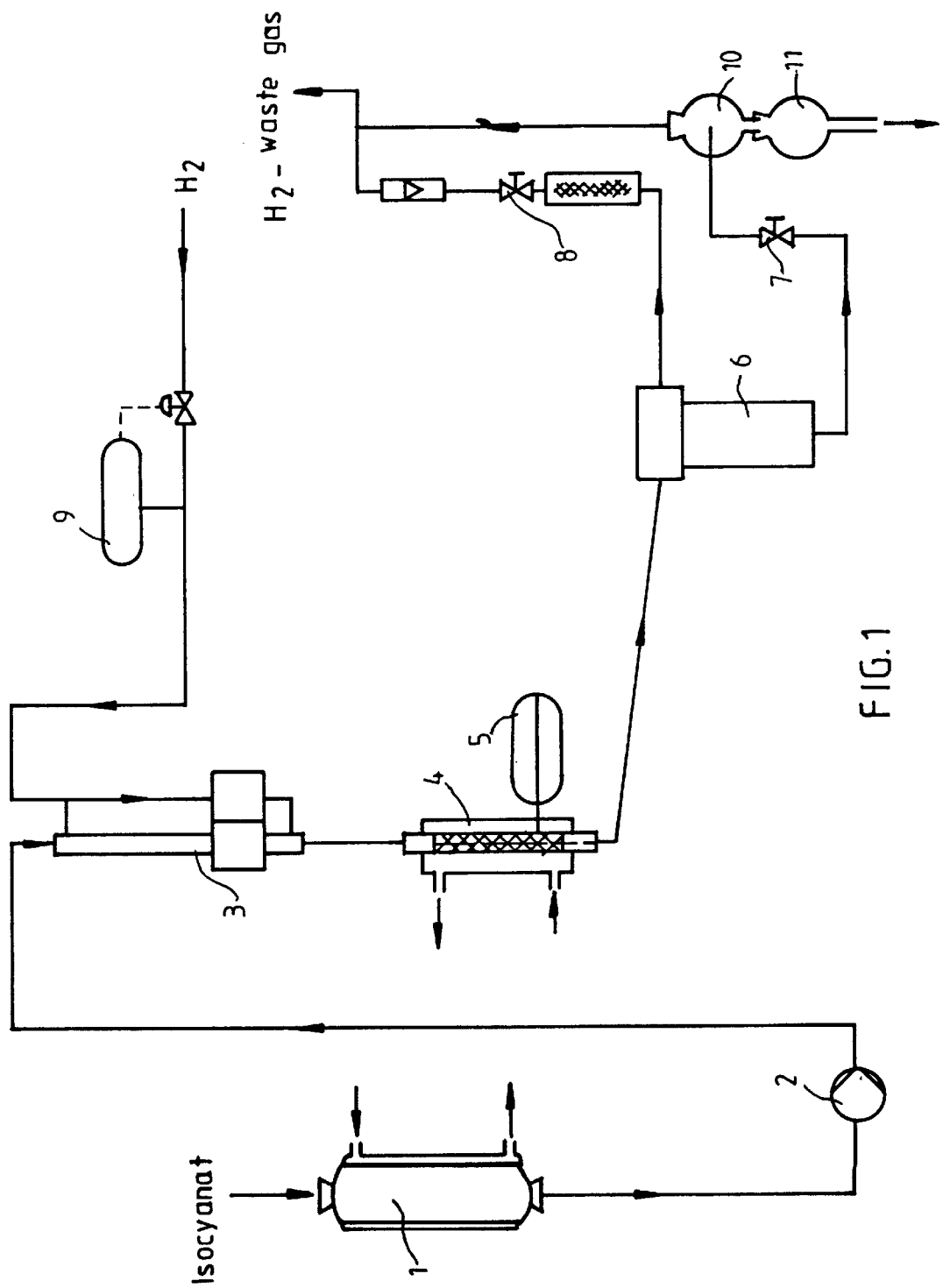
FIG. 1 illustrates an apparatus useful for the continuous hydrogen treatment of one or more isocyanates in accordance with the present invention.

The present invention is directed to a process for the preparation of isocyanates or isocyanate mixtures which are substantially free of color-imparting components. In this process, the amine corresponding to the desired isocyanate is phosgenated and the resultant isocyanates or isocyanate mixtures are subjected to a hydrogen treatment at a pressure of from about 3 to about 150 bar and a temperature of 100 to 180° C. in the presence of a catalyst for from about 15 minutes to about 4 hours.

The hydrogen treatment is performed at a pressure of from about 3 to about 150 bar, preferably from about 30 to about 100 bar.

The temperature may be from about 100 to about 180° C., preferably from about 140 to 160° C. during the hydrogen treatment.

Catalysts useful in the process of the present invention include any of the known hydrogenation catalysts. Catalysts which are particularly preferred include: platinum, palladium, ruthenium, rhodium, chromium, manganese, cobalt, nickel, silver, gold and mixtures thereof. The catalyst is generally used on a support in an amount of from about 0.1 to about 6.0% by weight, relative to the total weight of catalyst support. The preferred catalyst supports include activated carbon, aluminum oxide, spinels and mixed oxides with a specific surface area of from about 8 to about 1,000 $m^2/g$. Examples of suitable spinels or mixed oxides include $Me^{II}Me^{III}_2O_4$ and $Me^{I}_2Me^{III}_2O_4$ where $Me^{I}$=Li, $Me^{II}$=Mn, Zn, Co, Fe and Mg and $Me^{III}$=Al, Cr and Fe.

The catalysts are preferably applied to the support as aqueous solutions of salts of the metal, dried under vacuum and reduced to the metal in a stream of hydrogen at temperatures of >300° C.

Hydrogen/inert gas mixtures in which hydrogen is present in a proportion by volume of from about 3 to about 90% by volume may be used instead of pure hydrogen.

Preferably, solvent-free isocyanates or isocyanate mixtures with a viscosity of from about 8 to about 4,000 mPa.s at 25° C. or solutions of isocyanates or isocyanate mixtures in monochlorobenzene are treated with hydrogen in accordance with the present invention. Isocyanates or isocyanate mixtures of the diphenylmethane series, toluylenediisocyanates and mixtures thereof are particularly preferred isocyanates for the hydrogen treatment of the present invention.

Catalytic hydrogenation (EP 372 993) of organic compounds frequently takes place at elevated temperatures (>200° C.), with elevated hydrogen pressures (200 to 390 bar) and high hydrogen consumptions. In the process of the present invention, an extremely small amount of hydrogen is consumed. The process of the present invention is not, therefore, the same as the generally known hydrogenation processes.

To remove color-imparting impurities from isocyanates in accordance with the process of the present invention, it is possible to use a mixture of, for example, 5% hydrogen and the remainder an inert gas (e.g., nitrogen) at pressures of from about 3 to about 5 bar. Such mixtures make it possible to conduct the process of the present invention in a plant under conditions outside of the explosive range for hydrogen. In addition, materials which are resistant to high pressures of hydrogen need not be used to construct the plant.

The isocyanates or isocyanate mixtures prepared by the process according to the invention are particularly useful for the production of light-colored polyurethane foams.

The invention is further illustrated but is not intended to be limited by the following examples in which all parts and percentages are by weight unless otherwise specified.

EXAMPLES

Experimental Procedure

A: Hydrogen treatment was carried out in a 250 ml shaker autoclave with 25 ml of catalyst and 100 ml of MDI. The hydrogen pressure in the autoclave was variable from 200 bar to 6 bar. The product temperature could be adjusted from 20 to 200° C. After placing the MDI in the autoclave, the hydrogen pressure was adjusted, the autoclave was sealed and heated up over about 45 to 60 minutes and was then held at that temperature for about 45 to 60 minutes.

Afterwards, cooling took place over about 45 to 60 minutes. An expansion in volume occurred during the three hours of treatment, which led to a higher $H_2$ pressure in the autoclave.

B: Continuously operated hydrogen treatment was carried out in the apparatus shown in FIG. 1. Isocyanate was pumped out of the storage vessel 1 via pressure pump 2 into the metering device 3. Hydrogen from a storage container was reduced to the desired pressure via the pressure control valve 9. Both streams were passed through the reaction vessel 4, which contained 60 ml of catalyst and was heated to 200° C. via a control unit 5. The isocyanate treated with hydrogen was separated out in trap 6 and transferred outward via vessels 10 and 11. The hydrogen was expanded via valve 8 and removed as waste gas or recycled to the process.

Analytical Determination of the Color of MDI

Assessment of the color of polymeric MDI and its changes following hydrogen treatment was done by measuring the absorbance of a solution of 2 g of MDI in 100 ml of monochlorobenzene at A=520 nm and A=430 nm in a photometer (Digital Photometer LP 1W supplied by Lange GmbH, Berlin). This method was suitable for the rapid assessment of MDI. Color assessment of monomeric MDI was done by determining the Hazen color (DIN 53 409).

A more accurate method of determination is by measuring the transparency to light of the particular MDI samples with a path-length of 1 mm. Instead of the absorbance, the transmission spectrum is measured. In this instance, the percentage transmission of a non-treated sample and one treated with hydrogen may be compared better at different wavelengths. No solvent is used in this method of determination. On comparing the spectra, the degradation of color-imparting components may be indicated by a higher transparency, expressed as a percentage. The transparency may be used as a measure of the concentration of color-imparting impurities because, as is known, colorless liquids have virtually 100% transparency.

Isocyanates

Isocyanate A

A commercially available MDI with a viscosity of 200±20 mPa.s at 25° C. and an NCO content of 31.5%.

Isocyanate B

An isocyanate with an above-average depth of color in the corresponding polyurethane foam. It was a start-up product. The MDI was composed of about 90% two-ring MDI in which about 50% by weight was 4,4'-MDI, about 40% by weight was 2,4'-MDI and about 10% by weight was 2,2'-MDI. The viscosity was about 25 mPa.s at 25° C. and the NCO content was 32.0%.

Isocyanate C

An MDA with about 50 to 55% two-ring MDA prepared by known methods was phosgenated in o-dichlorobenzene as solvent. Working up of the phosgenated crude product and separation of the solvent from the MDI took place on a separating column in which all of the o-dichlorobenzene solvent was distilled off at the head. Viscosity of the MDI: 320 mPa.s at 25° C., NCO content: 30.7%.

Isocyanate D

A distillation residue which was produced during the preparation of toluylenediisocyanate was processed by mixing with MDI. The resulting soluble TDI-MDI mixture had a viscosity of 520 mPa.s at 25° C. and an NCO content of about 28.5%. Without any treatment, the mixture produced a dark brown/grey polyurethane rigid foam.

Isocyanate E

From an MDI containing about 70% two-ring MDI a fraction of 30% of monomeric MDI with a concentration of 4,4'-MDI of about 94% by weight and a concentration of 2,4'-MDI of about 5.5% by weight and a concentration of 3-ring MDI of about 0.5% was separated under vacuum. This crude monomeric MDI was dissolved in monochlorobenzene in the ratio of 1:1. The 50% strength MDI/chlorobenzene solution was subjected to a hydrogen treatment.

Catalysts

Catalyst A 200 g of a commercially available $\alpha$-$Al_2O_3$ with a specific surface area of 8 $m^2$/g and a particle diameter of 3 to 6 mm were soaked with a solution which had been prepared from 12.4 g of $Co(NO_3)_2.0.6H_2O$ 18.3 g of $Mn(NO_3)_2.0.4H_2O$ 3.2 g of $AgNO_3$ and 86 g of water.

The soaked aluminum oxide was dried for 18 hours at 120° C. under a water jet vacuum and then held at 400° C. for 3 hours. The catalyst support obtained in this way was soaked with a solution which had been prepared from 6.52 g $Ru(NO_3)_3$ and 75 g of water.

After renewed drying, the catalyst was reduced for 3 hours in a stream of hydrogen at 300° C. Finally, the catalyst was washed free of nitrate with distilled water and then dried again.

Catalyst B

Activated carbon impregnated with 5% by weight of Pd was chosen as the catalyst. A 4 mm granular activated charcoal was used to prepare the Pd catalyst, this having been prepared from hard coal and possessing a BET surface area of 1,000 $m^2$/g.

Catalyst C 150 g of a commercially available $\alpha$-$Al_2O_3$ with a specific surface area of 8 $m^2$/g and a particle diameter of 3 to 6 mm were soaked with a solution which had been prepared from 3.7 g of $H_2PtCl_6$ solution (30% Pt)

3.1 g of $RuCl_3$ and 62 g of water.

The soaked aluminum oxide was dried at 120° C. for 18 hours and then reduced for 3 hours in a stream of hydrogen at 370° C. The catalyst was then ready for use.

Catalyst D 200 g of a commercially available γ-$Al_2O_3$ with a specific surface area of 350 m²/g and a particle diameter of 2 to 5 mm were soaked with a solution which had been prepared from 6.68 g of $HAuCl_4$ solution (30%) and 70 g of water.

The soaked aluminum oxide was dried at 120° C. under a water jet vacuum and then activated for 3 hours at 380° C. in a stream of hydrogen.

Finally, the catalyst was soaked with a solution which had been prepared from 2 g of NaOH and 35 g of water. After further drying, the catalyst was ready for use.

The resulting chlorobenzene solution was distilled under nitrogen under a water jet vacuum until it was free of chlorobenzene and then distilled at 1 mbar pressure and about 180° C.

The same 50% strength solution of monomeric MDI in chlorobenzene was distilled directly until it was free of chlorobenzene, in the same way as above, and then distilled at 1 mbar pressure and about 180° C. The color was assessed by determining the Hazen color, using a 50% strength solution in monochlorobenzene as the standard.

Monomeric MDI, distilled=80 Hazen

Monomeric MDI, treated with hydrogen, distilled=40 Hazen

TABLE 1

| | Absorbance without treatment | | Absorbance with hydrogen treatment | | Transparency without hydrogen treatment (%) | | | | Transparency with hydrogen treatment (%) | | | | Hazen color without hydrogen | Hazen color with hydrogen treatment |
|---|---|---|---|---|---|---|---|---|---|---|---|---|---|---|
| | A 430 | A 520 | A 430 | A 520 nm | 450 nm | 500 nm | 550 nm | 600 nm | 450 nm | 500 nm | 550 nm | 600 nm | | |
| Example 1 | 0.28 | 0.046 | 0.21 | 0.020 | 10 | 42 | 63 | 74 | 13 | 50 | 72 | 78 | | |
| Example 2 | 0.575 | 0.440 | 0.068 | 0.013 | 3.5 | 6 | 17.3 | 40 | 30 | 63 | 74 | 80 | | |
| Example 3 | 0.869 | 0.253 | 0.487 | 0.088 | 0 | 1.7 | 6.6 | 20 | 0.6 | 14.5 | 40 | 60 | | |
| Example 4 | 1.352 | 0.435 | 1.068 | 0.277 | | | | | | | | | | |
| Example 5 | | | | | | | | | | | | | 80 | 40 |

TESTS

Example 1

123 g of Isocyanate A were placed in the autoclave described above in Procedure A, together with 25 ml of Catalyst A, and treated with hydrogen at a pressure of 30 bar and a temperature of 160° C. in accordance with Procedure A.

Example 2

Isocyanate B was treated with hydrogen in a continuously running test in the unit shown in FIG. 1 in accordance with Procedure B. The amount of Catalyst B was 60 ml (23.5 g). During the continuous test, the hydrogen pressure was on average 120 bar and the hydrogen throughput was 30 l/h. The temperature of the MDI was 140° C. The amount handled was about 35 g of MDI per hour.

Example 3

123 g of Isocyanate C were treated in the autoclave described above in Procedure A at 100 bar pressure of hydrogen and 160° C., in the presence of 25 ml of Catalyst C in accordance with Procedure A.

Example 4

123 g of Isocyanate D were treated with 25 ml of Catalyst A at 170° C. and a hydrogen pressure of 60 bar, in the autoclave described above in accordance with Procedure A.

Example 5

100 ml of a 50% strength solution of monomeric MDI in chlorobenzene were treated at 140° C. and 30 bar pressure of hydrogen in the autoclave described above, using Catalyst D.

What is claimed is:

1. A process for the production of an isocyanate or a mixture of isocyanates which is substantially free of color imparting material comprising treating a phosgenation product of an amine with hydrogen at a pressure of from about 3 to about 150 bar at a temperature of from about 100 to about 180° C. for from about 15 minutes to about 4 hours in the presence of a catalyst.

2. The process of claim 1 in which hydrogen at a pressure of from about 30 to about 100 bar is used.

3. The process of claim 1 in which the treatment is carried out at a temperature of from about 140 to about 160° C.

4. The process of claim 1 in which the catalyst used is selected from the group consisting of platinum, palladium, ruthenium, rhodium, chromium, manganese, cobalt, nickel, silver, gold, compounds of each of these metals and mixtures thereof.

5. The process of claim 4 in which the catalyst is present on a support material.

6. The process of claim 5 in which the catalyst is present in an amount of from about 0.1 to about 6.0% relative to the total weight of catalyst support.

7. The process of claim 5 in which the support material is selected from the group consisting of activated carbon, aluminum oxide, spinels, mixed oxides and mixtures thereof.

8. The process of claim 7 in which the support material has a specific surface area of from about 8 to about 1000 m²/g.

9. The process of claim 1 in which an inert gas is used in addition to hydrogen.

10. The process of claim 9 in which from about 3 to about 90% by volume of the total amount of hydrogen plus inert gas is hydrogen.

11. The process of claim 1 in which any solvent present in the phosgenation product is removed prior to treatment with hydrogen.

12. The process of claim 1 in which the phosgenation product to be treated has a viscosity of from about 8 to about 4,000 mpa.s at 25° C.

13. The process of claim 1 in which the phosgenation product to be treated is in solution.

14. The process of claim 1 in which the phosgenation product to be treated is a mixture of isocyanates in monochlorobenzene.

15. The process of claim 1 in which the phosgenation product to be treated is selected from isocyanates of the diphenylmethane series, toluylene diisocyanates and mixtures thereof.

16. A process for the production of a light-colored polyurethane foam comprising reacting the isocyanate produced by the process of claim 1 with a polyisocyanate reactive material in the presence of a catalyst.

* * * * *